(12) United States Patent
Tannian et al.

(10) Patent No.: US 8,064,570 B2
(45) Date of Patent: Nov. 22, 2011

(54) HAND-HELD XRF ANALYZER

(75) Inventors: Bridget Tannian, Hyde Park, MA (US); Brad Hubbard-Nelson, Concord, MA (US); Alfred Oleru, Quincy, MA (US)

(73) Assignee: Innov-X-Systems, Inc., Woburn, MA (US)

( * ) Notice: Subject to any disclaimer, the term of this patent is extended or adjusted under 35 U.S.C. 154(b) by 0 days.

(21) Appl. No.: 11/642,808

(22) Filed: Dec. 20, 2006

(65) Prior Publication Data
US 2008/0152079 A1 Jun. 26, 2008

(51) Int. Cl.
*G01N 23/223* (2006.01)

(52) U.S. Cl. .................. 378/45; 378/44; 378/47; 378/49

(58) Field of Classification Search .................... 378/44, 378/45, 47, 49, 53
See application file for complete search history.

(56) References Cited

U.S. PATENT DOCUMENTS

| | | | |
|---|---|---|---|
| 4,599,741 A | 7/1986 | Wittry | |
| 4,848,590 A | 7/1989 | Kelly | |
| 5,236,092 A | 8/1993 | Krotkov et al. | |
| 5,260,576 A | 11/1993 | Sommer, Jr. et al. | |
| 5,314,071 A | 5/1994 | Christian et al. | |
| 5,329,569 A * | 7/1994 | Spielman | 378/161 |
| 5,414,195 A | 5/1995 | Peterson et al. | |
| 5,424,959 A | 6/1995 | Reyes et al. | |
| 5,481,109 A | 1/1996 | Ninomiya et al. | |
| 5,563,929 A | 10/1996 | Connolly et al. | |
| 5,570,406 A | 10/1996 | Komatani | |
| 5,657,363 A | 8/1997 | Hossaim et al. | |
| 5,663,997 A | 9/1997 | Willis et al. | |
| 6,266,390 B1 | 7/2001 | Sommer, Jr. et al. | |
| 6,314,158 B1 * | 11/2001 | Shiota et al. | 378/48 |
| 6,459,767 B1 * | 10/2002 | Boyer | 378/121 |
| 6,519,315 B2 | 2/2003 | Sommer, Jr. et al. | |
| 6,855,930 B2 * | 2/2005 | Okuda et al. | 250/310 |
| 6,882,701 B2 * | 4/2005 | Ferrandino et al. | 378/44 |
| 6,888,917 B2 | 5/2005 | Sommer, Jr. et al. | |
| 6,909,770 B2 * | 6/2005 | Schramm et al. | 378/45 |
| 7,020,238 B1 * | 3/2006 | Kantonen et al. | 378/44 |

(Continued)

FOREIGN PATENT DOCUMENTS

CA 1110996 10/1981

(Continued)

OTHER PUBLICATIONS

ASOMA Instruments, Inc., PET/PVC Sorter, Model VS-2*, Specification Sheet, ASOMA Instruments, Inc., Austin, Texas, 2 pages, Apr. 20, 1993.

(Continued)

*Primary Examiner* — Hoon Song
*Assistant Examiner* — Mona M Sanei
(74) *Attorney, Agent, or Firm* — Iandiorio Teska & Coleman

(57) ABSTRACT

A hand-held XRF analyzer including an x-ray source for emitting x-rays through a window to a sample. A detector behind the window is responsive to x-rays irradiated by the sample. A controlled volume about the x-ray source and the detector is maintained in a vacuum or a predetermined purge condition for a predetermined amount of time for increasing the sensitivity of the analyzer. A processor is responsive to the detector for analyzing the spectrum of irradiated x-rays and responsive to a pressure sensor for detecting a pressure change inside the controlled volume. The processor is configured to detect if the vacuum or the predetermined purge condition has been compromised.

4 Claims, 4 Drawing Sheets

U.S. PATENT DOCUMENTS

| | | | |
|---|---|---|---|
| 7,099,433 B2 | 8/2006 | Sommer | |
| 2003/0053589 A1 | 3/2003 | Ikeshita et al. | |
| 2005/0078786 A1 | 4/2005 | Sommer, Jr. et al. | |
| 2005/0129174 A1* | 6/2005 | Sipila et al. | 378/44 |
| 2005/0226373 A1* | 10/2005 | Trombka et al. | 378/44 |
| 2005/0251118 A1* | 11/2005 | Anderson et al. | 606/9 |
| 2006/0013360 A1 | 1/2006 | Sommer, Jr. et al. | |
| 2006/0034425 A1* | 2/2006 | Unger et al. | 378/125 |
| 2006/0239401 A1 | 10/2006 | Sommer, Jr. et al. | |
| 2006/0262900 A1 | 11/2006 | Sipila et al. | |
| 2007/0030953 A1 | 2/2007 | Sommer, Jr. et al. | |
| 2007/0269003 A1* | 11/2007 | Puusaari et al. | 378/44 |
| 2008/0192897 A1* | 8/2008 | Piorek et al. | 378/98.8 |

FOREIGN PATENT DOCUMENTS

| | | | |
|---|---|---|---|
| EP | 0960092 | | 12/1983 |
| JP | 01156646 A | | 6/1989 |
| JP | 02190752 | * | 6/1990 |
| SU | 952384 | | 12/1979 |
| WO | WO 01/22072 A1 | | 3/2001 |
| WO | WO 2005/086616 A2 | | 9/2005 |
| WO | WO 2006/094061 A1 | | 9/2006 |
| WO | WO 2007/089362 A2 | | 8/2007 |
| WO | WO 2008/017075 A2 | | 2/2008 |

OTHER PUBLICATIONS

Dinger, Peter, "Automatic Sorting For Mixed Plastics", BioCycle, Mar. 1992, 2 pages (unnumbered).

* cited by examiner

HAND-HELD XRF ANALYZER

FIELD OF THE INVENTION

This invention relates generally to a hand-held x-ray fluorescence (XRF) analyzer and more particularly, to an improved hand-held XRF analyzer that provides a desired condition of a controlled volume about the x-ray source and the detector to improve sensitivity of the analyzer and which alerts the operator if the desired condition has been compromised.

BACKGROUND OF THE INVENTION

Hand-held XRF analyzers are used to detect elements present in a sample. A typical hand-held XRF analyzer includes an x-ray source for directing x-rays to the sample and a detector responsive to the x-rays emitted from the sample. An analyzer processes the output signals produced by the detector and divides the energy levels of the detected x-ray photons into several energy subranges by counts of the number of x-ray photons detected to produce a graph depicting the x-ray spectrum of the sample.

Hand-held XRF analyzers are known. See, e.g., the applicants' co-pending applications, U.S. patent application Ser. No. 11/582,038 filed Oct. 17, 2006 entitled "XRF System with Novel Sample Bottle", and U.S. patent application Ser. No. 11/585,367 filed Oct. 24, 2006 entitled "Fuel Analysis System", by one or more common inventors hereof and all of the same assignee, incorporated by reference herein. See also U.S. Pat. Nos. 6,501,825; 6,909,770; 6,477,227; and 6,850,592, all of which are incorporated by reference herein. Using a hand-held XRF analyzer, an operator can detect whether certain elements are present in sample for use in such applications as, inter alia, security and law enforcement, environmental applications, artistic and historic works, biomedical and pharmaceutical applications, process chemistry, and the like. Another key use of hand-held XRF analyzers is to detect elements listed by the European Union Directive Restriction on the Use of Certain Hazardous Substances (RoHs). This Directive restricts the use of certain hazardous substances, such as lead ($P_b$), mercury ($H_g$), cadmium ($C_d$), chromium ($C_r$) and Bromine ($B_r$), and the like, in manufactured electrical and electronic equipment.

In operation, it is difficult to analyze the low energy x-rays emitted by the electrons of elements having lower atomic numbers, e.g., elements between sodium (Na) and chlorine (Cl). This is because the lower energy of these x-rays is typically reabsorbed by the ambient atmosphere (e.g., air) or the material itself. In order to accurately analyze and detect these lower atomic number elements, the air between the analyzer window and the detector must be removed. This is done either by creating a vacuum or performing a helium (He) purge whereby the helium displaces the air between the analyzer window and the detector. The vacuum or the purge condition prevents the lower energy x-rays from being absorbed into the ambient atmosphere and increases the sensitivity of the XRF analyzer.

However, conventional hand-held XRF analyzers are limited to providing a vacuum or a purge condition, but not both, in a chamber containing the analyzer components. Conventional hand-held XRF analyzers also typically employ a large chamber which increases the time required to create the vacuum or purge condition. The large volume also requires the operator of the analyzer to carry a pump that continuously maintains the desired vacuum or purge condition.

For example, U.S. Pat. No. 6,909,770 to Schramm et al., incorporated by reference herein, relies on a vacuum chamber attachment mounted to the end of a portable XRF analyzer. The sample to be analyzed is placed inside the chamber and the entire volume is evacuated. This approach has the disadvantage of requiring a sample to be removed and placed into the chamber rather than allowing samples to be tested in-situ. The design also requires a larger volume for the vacuum, thus requiring a larger pump which reduces the overall portability of the XRF analyzer.

Other conventional XRF analyzers that utilize a helium purge require an external helium supply. In this design, the operator wears a tank of compressed helium in a backpack with a gas line running into the front snout of the XRF analyzer. The helium gas is continuously flushed through the volume inside the XRF analyzer that includes the air path between the analysis window and the detector. Such designs are cumbersome and difficult to use.

Another conventional XRF analyzer is disclosed in U.S. Pat. No. 7,065,174 to Sipilä, et al., incorporated by reference herein. The XRF analyzer as disclosed by Sipilä, et al. utilizes a removable gas-filled chamber placed inside the volume about the x-ray source, the sample and the detector. The chamber is filled with an appropriate gas, e.g., helium, and hermetically sealed. The chamber is locked into place and used for a period of time. The drop-in chamber is intended to be field replaceable by the end-user. However, the analyzer as disclosed by Sipilä does not offer a way to replenish the purge gas. The chamber must be removed, purged, and replaced. The removal process may compromise expensive and sensitive detector and x-ray tube components situated close by. In practice, most customers do not have the skills to perform this replacement in the field. Thus, a more advantageous design would provide the analyzer with the ability to hold the purge gas for a period of time and alert the operator when the quantity of purge gas was inadequate. Then, the operator could simply connect to a local source of helium gas. However, the analyzer as disclosed by Sipilä et al. fails to teach or disclose these features.

Thus, the conventional hand-held XRF analyzers discussed above are not designed to provide either a vacuum or purge condition as needed and cannot determine if the vacuum or purge condition is being maintained while the analyzer is in operation. Moreover, when the vacuum chamber is integrated with the various components of the analyzer, if the chamber or any of the components fail while the analyzer in operation, the components cannot easily be serviced by the operator in the field. Such a design also prevents the components of the analyzer from being easily upgraded.

BRIEF SUMMARY OF THE INVENTION

It is therefore an object of this invention to provide an improved hand-held XRF analyzer.

It is a further object of this invention to provide such a hand-held XRF analyzer which provides either a vacuum or a predetermined purge condition in a controlled volume about the x-ray source and the detector.

It is a further object of this invention to provide such a hand-held XRF analyzer which alerts the operator if the vacuum or the purge condition has been compromised.

It is a further object of this invention to provide such a hand-held XRF analyzer which maintains the vacuum or the purge condition for a predetermined amount of time.

It is a further object of this invention to provide such a hand-held XRF analyzer which eliminates the need for the operator to carry a pump or a tank of pressurized gas.

It is a further object of this invention to provide such a hand-held XRF analyzer which can test a sample in-situ.

It is a further object of this invention to provide such a hand-held XRF analyzer which reduces the time required to create the vacuum or the purge condition.

It is a further object of this invention to provide such a hand-held XRF analyzer which easily re-establishes the vacuum or the purge condition.

It is a further object of this invention to provide such a hand-held XRF analyzer which is serviceable and upgradeable in the field by skilled service engineers.

It is a further object of this invention to provide such a hand-held XRF analyzer which prevents damage to the electronics, x-ray tube, and detector when the analyzer is serviced in the field.

It is a further object of this invention to provide such a hand-held XRF analyzer which is easily upgradeable.

It is a further object of this invention to provide such a hand-held XRF analyzer which is easier to use.

The subject invention results from the realization that an improved hand-held XRF analyzer which quickly and easily provides either a vacuum or a predetermined purge condition in a controlled volume about the x-ray source and the detector in order to detect lower atomic number elements and which alerts the operator if the vacuum or the purge condition has been compromised and is serviceable and upgradeable in the field by skilled service engineers is effected with an x-ray source for emitting x-rays through a window to a sample. A detector behind the window is responsive to the x-rays radiated from the sample. A controlled volume about the x-ray source and the detector is maintained in either a vacuum or purge condition for a predetermined amount of time to increase the sensitivity of the analyzer. A processor responsive to the detector analyzes the spectrum of emitted x-rays to detect the low atomic number elements and is responsive to a pressure sensor that detects a pressure change inside the controlled volume. The processor is programmed to detect if the vacuum or predetermined purge condition has been compromised.

This invention features a hand-held XRF analyzer including an x-ray source for emitting x-rays through a window to a sample. A detector behind the window is responsive to x-rays irradiated by the sample. A controlled volume about the x-ray source and the detector is maintained in a vacuum or a predetermined purge condition for a predetermined amount of time for increasing the sensitivity of the analyzer. A processor is responsive to the detector for analyzing the spectrum of irradiated x-rays and responsive to a pressure sensor for detecting a pressure change inside the controlled volume. The processor is configured to detect if the vacuum or the predetermined purge condition has been compromised.

In one embodiment, the processor may be configured to detect a predetermined threshold intensity of argon in the controlled volume and provide an output signal indicating the predetermined purge condition has been compromised. The processor may provide an output signal when the pressure of the controlled volume changes indicating the vacuum has been compromised. The vacuum may be maintained for at least 2 hours. The predetermined purge condition may be maintained for at least 2 hours. The hand-held XRF analyzer may include a display responsive to the output signal for displaying an indication that the purge condition has been compromised. The hand-held XRF analyzer may include a display responsive to the output signal for displaying an indication that the vacuum has been compromised. The hand-held XRF analyzer may include a vacuum pump for creating the vacuum in the controlled volume. The hand-held XRF analyzer may include a purge subsystem for supplying a purge gas to the controlled volume for creating the predetermined purge condition in the controlled volume. The purge gas may be helium. The controlled volume may be created in a housing. The housing may be disposed between a top plate and a bottom plate. The housing may be removable. The housing may have a low volume. The hand-held XRF analyzer may include a removable window plate for housing the window. The window may be made of polyimide film or KAPTON® (a polyimide material).

The hand-held XRF analyzer may include an O-ring disposed between the housing and the x-ray source and an O-ring disposed between the detector and the housing for maintaining the vacuum or the predetermined purge condition for the predetermined amount of time. The processor may be programmed to detect the presence of one or more elements in the sample having low atomic numbers. The one or more elements may include elements having an atomic number in the range of about 11 to 17. The processor may be configured to adjust the vacuum pump to ensure the vacuum is being properly maintained. The processor may be configured to adjust the purge subsystem to ensure the predetermined purge condition is being properly maintained.

This invention also features a hand-held XRF analyzer including an x-ray source for emitting x-rays through a window to a sample. A detector behind the window is responsive to x-rays irradiated by the sample. A controlled volume about the x-ray source and the detector is maintained in a vacuum for a predetermined amount of time for increasing the sensitivity of the analyzer. A processor is responsive to the detector for analyzing the spectrum of irradiated x-rays and is responsive to a pressure sensor for detecting a pressure change inside the controlled volume. The processor is configured to detect if the vacuum has been compromised.

In one embodiment, the processor may provide an output signal when the pressure Of the controlled volume changes indicating the vacuum has been compromised. The vacuum may be maintained for at least 2 hours. The hand-held XRF analyzer may include a display responsive to the output signal for displaying an indication that the vacuum has been compromised. The hand-held XRF analyzer may include a vacuum pump coupled for creating the vacuum in the controlled volume. The controlled volume may be created in a housing. The housing may be disposed between a top plate and a bottom plate. The housing may be removable. The housing may have a low volume. The hand-held XRF analyzer may include a removable window plate for housing the window. The window may be made of polyimide film or of KAPTON® (a polyimide material). The hand-held XRF analyzer may include an O-ring disposed between the housing and the x-ray source and an O-ring disposed between the detector and the housing for maintaining the vacuum for the predetermined amount of time in the housing. The processor may be programmed to detect the presence of one or more elements in the sample having low atomic numbers. One or more elements may include elements having an atomic number in the range of about 11 to 17. The processor may be configured to adjust the vacuum pump to ensure the vacuum is being properly maintained.

This invention further features a hand-held XRF analyzer including an x-ray source for emitting x-rays through a window to a sample. A detector behind the window is responsive to x-rays irradiated by the sample. A controlled volume about the x-ray source and the detector is maintained in a predetermined purge condition for a predetermined amount of time for increasing the sensitivity of the analyzer. A processor is responsive to the detector for analyzing the spectrum of irradiated x-rays and configured to detect if the predetermined purge condition has been compromised.

In one embodiment, the processor may be configured to detect a predetermined threshold intensity of argon in the controlled volume and provide an output signal indicating the predetermined purge condition has been compromised. The predetermined purge condition may be maintained for at least 2 hours. The hand-held XRF analyzer may include a display responsive to the output signal for displaying the indication that the purge condition has been compromised. The hand-held XRF analyzer may include a purge subsystem for supplying a purge gas into the controlled volume for creating the predetermined purge condition in the controlled volume. The purge gas may be helium. The controlled volume may be created in a housing. The housing may be disposed between a top plate and a bottom plate. The housing may be removable. The housing may have a low volume. The hand-held XRF analyzer may include a removable window plate for housing the window. The window may be made of polyimide film or KAPTON® (a polyimide material). The hand-held XRF analyzer may include an O-ring disposed between the housing and the x-ray source and an O-ring disposed between the detector and the housing for maintaining the predetermined purge condition for the predetermined amount of time in the housing. The processor may be programmed to detect the presence of one or more elements in the sample having low atomic numbers. The one or more elements may include elements having an atomic number in the range of about 11 to 17. The processor may be configured to adjust the purge subsystem to ensure the predetermined purge condition is being properly maintained.

This invention also features a hand-held XRF analyzer including an x-ray source for emitting x-rays through a window to a sample. A detector behind the window is responsive to x-rays irradiated by the sample. A controlled volume about the x-ray source and the detector is maintained in a vacuum or a predetermined purge condition for a predetermined amount of time for increasing the sensitivity of the analyzer. A vacuum pump provides the vacuum in the controlled volume. A purge subsystem supplies a purge gas into the controlled volume to provide the predetermined purge condition in the controlled volume. A processor is responsive to the detector for analyzing the spectrum of irradiated x-rays and responsive to a pressure sensor for detecting a pressure change inside the controlled volume. The processor is programmed to detect if the vacuum or predetermined purge condition has been compromised.

This invention also features a method of detecting if a predetermined condition of a controlled volume of a hand-held XRF analyzer is being properly maintained including establishing a controlled volume about an x-ray source and a detector, maintaining the controlled volume in a vacuum or a predetermined purge condition for a predetermined amount of time, detecting if the vacuum or the predetermined purge condition has been compromised.

In one embodiment, the method includes the step of detecting a predetermined threshold intensity of argon in the controlled volume to determine if the predetermined purge condition has been compromised. The method may include the step of detecting a pressure change in the controlled volume to determine if the vacuum has been compromised.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
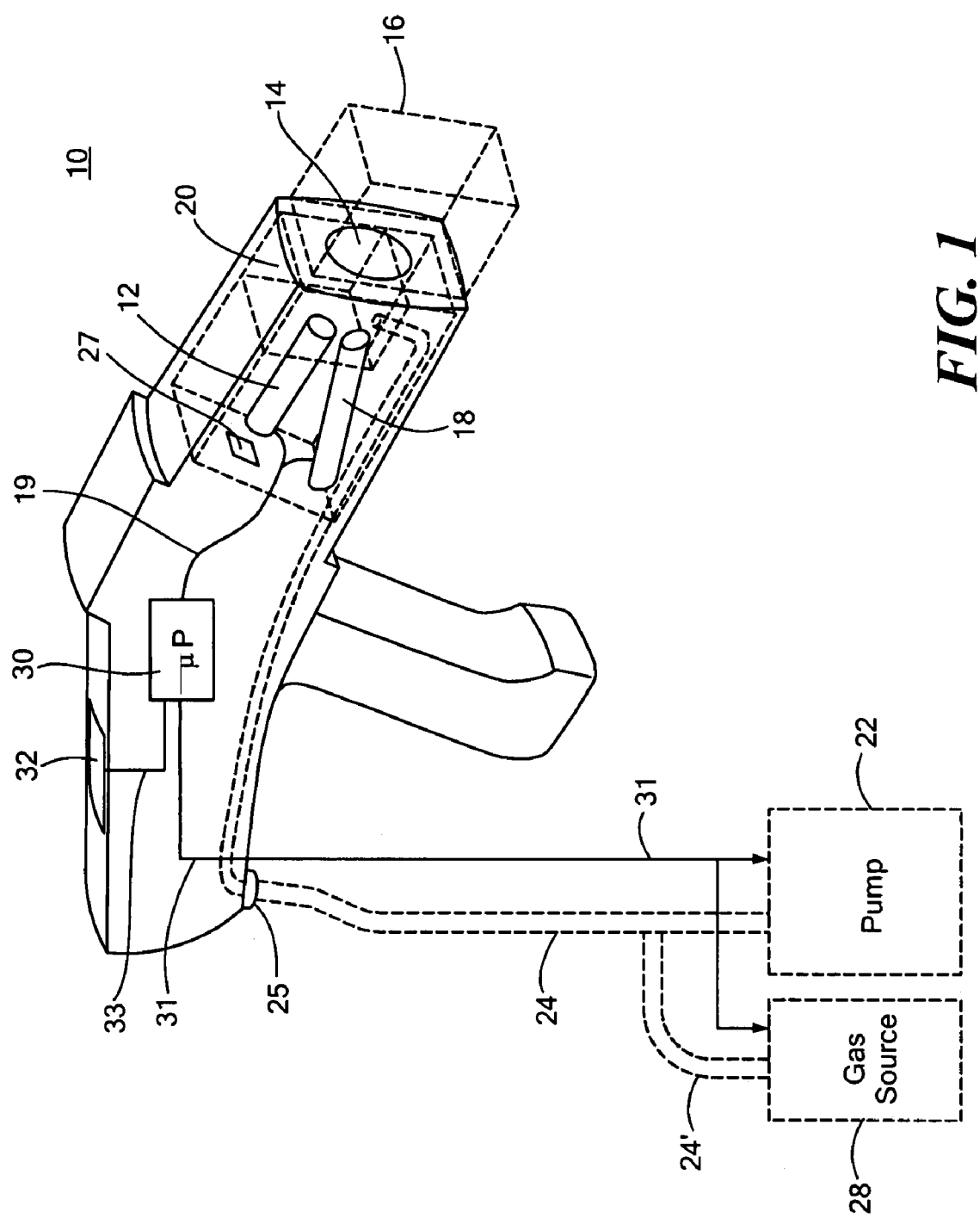
FIG. 1 is simplified three-dimensional view of one embodiment of the hand-held XRF analyzer of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

In one example, hand-held XRF analyzer 10, FIG. 1 of this invention includes x-ray source 12, e.g., an x-ray tube, for emitting x-rays through window 14 to sample 16. Detector 18 behind window 14 is responsive to x-rays radiated by sample 16. Controlled volume 20 about x-ray source 12 and detector 18 is maintained in either a vacuum or predetermined purge condition for a predetermined amount of time, e.g., at least 2 hours, discussed in further detail below. The vacuum or purge condition in controlled volume 20 increases the sensitivity of analyzer 10 to detect, inter alia, elements having lower atomic numbers, such as those elements between sodium (Na, atomic number 11) and chlorine (Cl, atomic number 17). Preferably, controlled volume 20 is created in housing 21, FIG. 2, where like parts have been given like numbers. The vacuum in housing 21 is typically created with pump 22, FIG. 1 by hose 24 connected to valve 25 coupled to vacuum tube 54, FIG. 2 which is attached to vacuum fitting 23 on housing 21. Pump 22 is typically attached for about 10 seconds to create the vacuum and then removed when analyzer 10 is used for testing. The predetermined purge condition, e.g., a helium purge, in controlled volume 20 in housing 21 is typically created by flushing controlled volume 20 with helium using gas source 28, FIG. 1, e.g., a tank of compressed helium, coupled to hose 24' connected to valve 25. Other suitable gases known by those skilled in the art may be used to create the predetermined purge condition in controlled volume 20. Controlled volume 20 is typically flushed for about 10 seconds to refresh the purge gas. Then, gas source 28 of compressed gas is removed when the analyzer is used for testing. Valve 25 is coupled to gas tube 56, FIG. 2 which is attached to gas inlet 40 connected to housing 21. The desired vacuum or purge condition in controlled volume 20 is preferably maintained for at least 2 hours to provide hand-held XRF analyzer 10 with the ability to more accurately analyze and test for elements having lower atomic numbers before refreshing the vacuum or re-purging with purge gas. Maintaining controlled volume 20 at the vacuum or purge condition for at least 2 hours eliminates the need for an operator to carry a pump, e.g., pump 22, FIG. 1, to maintain the desired vacuum or the need for the operator to carry a tank of compressed gas, e.g., gas source 28, to maintain a desired purge condition. Thus, hand-held XRF analyzer 10 is less cumbersome and easier to use than conventional hand-held XRF analyzers discussed in the Background Section above.

Processor 30, FIG. 1 is responsive to detector 18 by line 19 and analyzes the spectrum of irradiated x-rays from sample 16. Processor 30 is also responsive to pressure sensor 27 inside controlled volume 20. Processor 30 is programmed to detect if the desired vacuum or purge condition in control volume 20 has been compromised.

For example, when a predetermined purge condition is created in controlled volume 20, processor 30 measures a predetermined threshold intensity of argon in controlled volume 20. A known upper limit of argon intensity as a percentage of argon intensity of air at standard atmospheric pressure, e.g., 20% of the argon concentration present compared to air at standard atmospheric pressure, is determined during factory calibration (threshold intensity) that dictates when the purge condition is no longer acceptable. When processor 30 senses an argon intensity in excess of the threshold intensity, processor 30 provides an error message by line 33 to display 32 which indicates the desired purge condition in controlled volume has been compromised. Argon is a naturally occurring element in the ambient atmosphere. If argon is present above the predetermined threshold intensity value in controlled volume 20, the desired purge condition in controlled volume 20 has been compromised. This can lead to inaccurate measurements. Thus, hand-held XRF analyzer 10 quickly alerts an operator of a compromised purge condition. Once aware of the compromised purge condition, the operator can re-establish the desired purge condition using gas source 28 or have XRF analyzer repaired by skilled service engineers.

Although as discussed above, detecting the presence of argon in the controlled volume is used to determine if the predetermined purge condition has been compromised, this is not a necessary limitation of this invention, as other elements and substances known by those skilled in the art may be utilized to determine if the predetermined purge condition in the controlled volume has been compromised.

Figure 3:
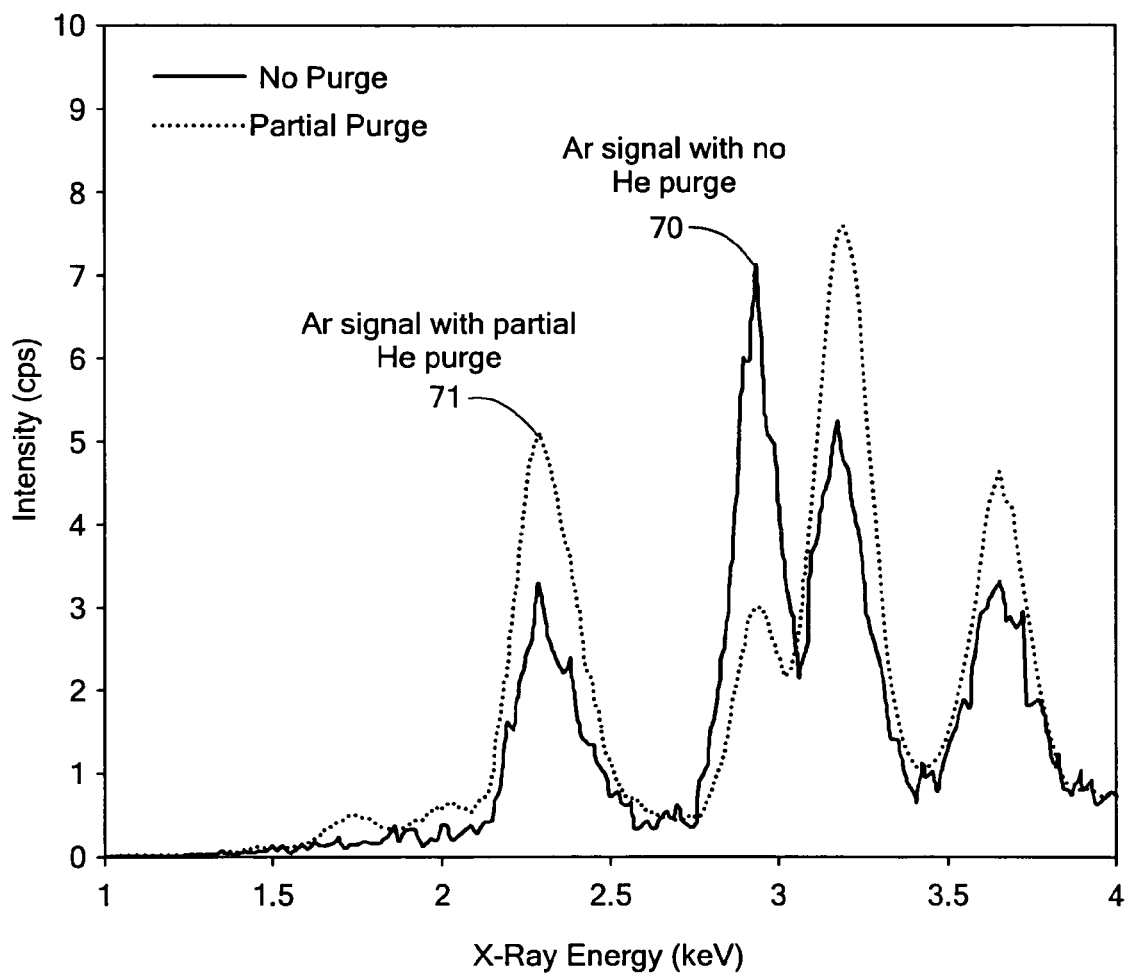
FIG. 3 is a graph of an example spectrum generated by the hand-held XRF analyzer shown in FIGS. 1 and 2 depicting the detection of argon present in the controlled volume about the x-ray source and detector.

FIG. 3 shows an example of a spectrum that is typically generated by Processor 30 and shows the detection of an argon peak, e.g., an argon peak 70 in controlled volume 20 that indicates the purge condition has been compromised. Peak 71 shows at a point when the helium purge has worsened such that the argon concentration is about 20 percent higher than the threshold intensity. These spectra demonstrate that the argon intensity is a very sensitive probe to determine the quality of the predetermined purge condition in controlled volume 20.

When a vacuum is created in controlled volume 20, FIG. 1, pressure sensor 27, is used to measure the pressure inside controlled volume 20. Processor 30 responds to a pressure change provided by pressure sensor 27 and provides an error signal by line 33 to display 32 that alerts the operator that the vacuum has been compromised.

Figure 2:
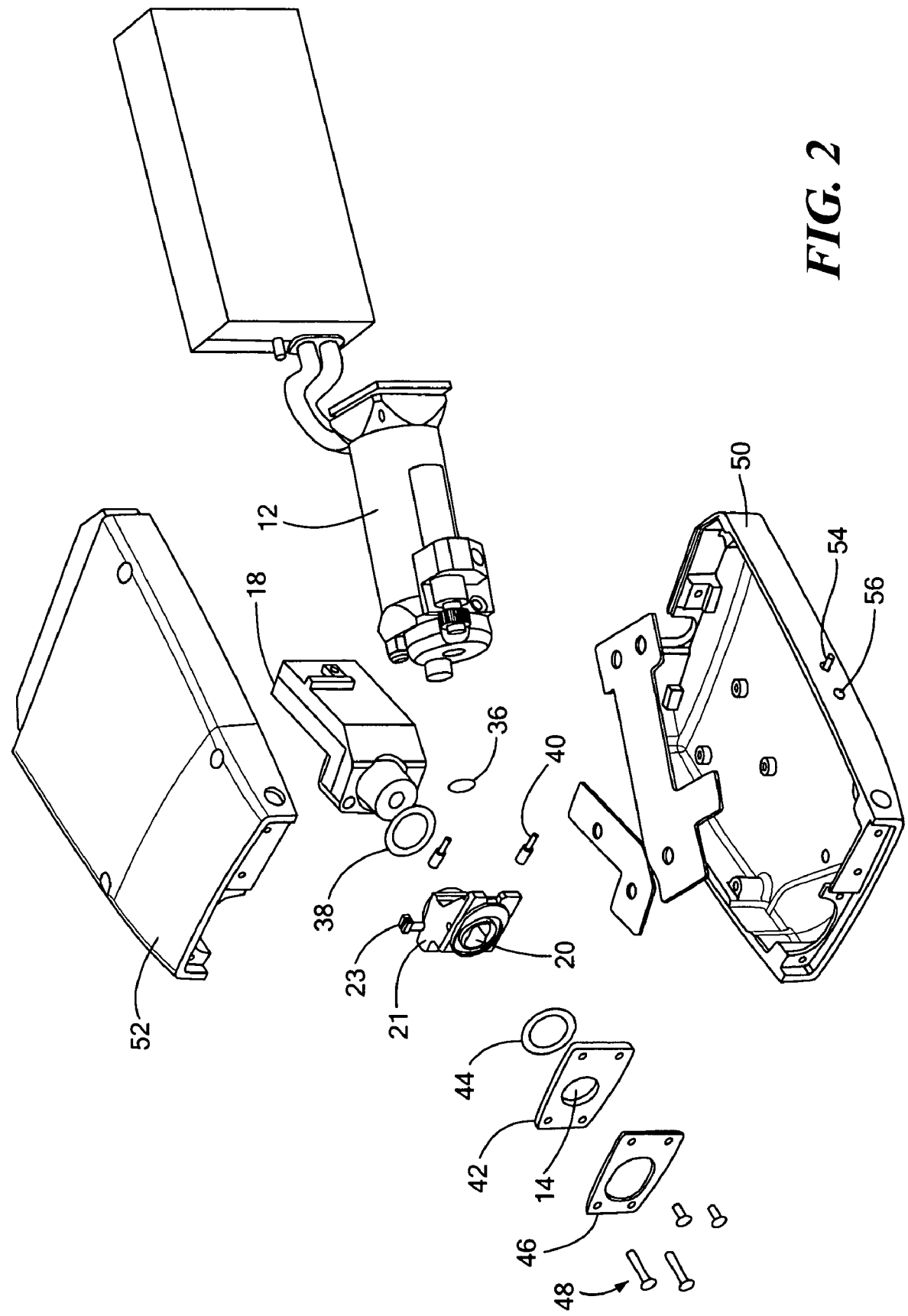
FIG. 2 is three-dimensional schematic diagram showing the further detail the components of the hand-held XRF analyzer shown in FIG. 1.
Figure 4:
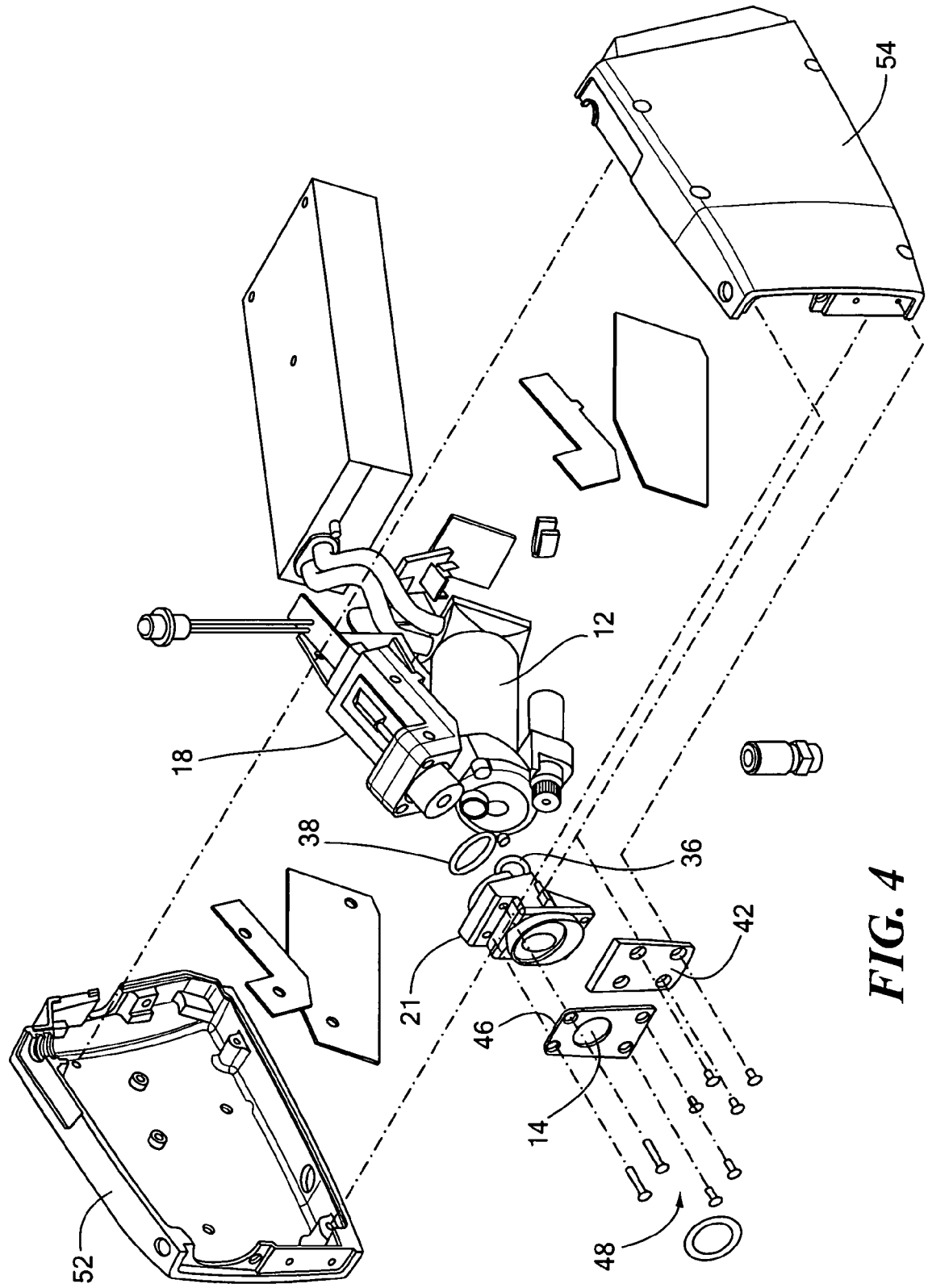
FIG. 4 is another three-dimensional schematic diagram showing the components of the hand-held XRF analyzer shown in FIGS. 1 and 2.

In a preferred embodiment, housing 21, FIGS. 2 and 4 is connected to x-ray source 12 with O-ring 36 disposed there between. Similarly, detector 18 is connected to housing 21 with O-ring 38 disposed there between. Such a design maintains the desired vacuum or purge condition in the controlled volume for a predetermined amount of time, e.g., at least 2 hours, as discussed above.

Face plate 42 with window 14, e.g., a window made of polyimide film, e.g., KAPTON® (a polyimide material), or similar type material, is attached to housing 21 using O-ring 44. Exterior plate 46 attaches to face plate 42 via screws 48. Bottom cover 50 and top cover 52 are disposed over the components described above. Thus, housing 21 is designed to be removed only by skilled service engineers. This prevents untrained operators from removing housing 21 and potentially damaging detector 18, x-ray source 12, and the complex electronics associated therewith, which can have an adverse impact on calibration and quality of the measurement of analyzer 10.

Ideally, housing 21 has a volume of about 0.05 cubic inches which is significantly smaller the volume of conventional hand-held XRF analyzers. This provides the ability for analyzer 10 to quickly create the desired vacuum or purge condition for controlled volume 20 inside housing 21, e.g., in less than about 10 seconds. The small volume of controlled volume 20 in housing 21 also holds the desired vacuum or purge conditions longer, thus further eliminating the need for the operator to carry a pump while in operation.

Although, as described above, hand-held XRF analyzer 10 typically does not require the operator to carry a pump, in one embodiment, an error message may be provided by processor 30, FIG. 1 by line 31 to pump 22 or gas source 28 that is used in feedback to maintain the vacuum or predetermined purge condition in controlled volume 20.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A hand-held XRF analyzer comprising:
   a housing defining a controlled volume;
   a port in the housing for drawing a vacuum in the controlled volume;
   a window including a film, the window in front of the controlled volume and sealed with respect to the housing;
   an x-ray source located external to the housing and sealed with respect to the housing for emitting x-rays first into the controlled volume and then through the window to a sample;

a detector external to the housing, sealed with respect to the housing, and responsive to x-rays irradiated by the sample passing through the window and into the controlled volume;

a processor responsive to the detector for analyzing irradiated x-rays and configured to determine if the vacuum in the controlled volume has been compromised; and a hand-held case enclosing the housing, source, detector, and processor.

2. The analyzer of claim 1 further including a pressure sensor responsive to the pressure in the controlled volume providing an output to the processor indicative of the pressure in the controlled volume to determine if the vacuum in the controlled volume has been compromised.

3. The analyzer of claim 2 further including a display for displaying an indication that the vacuum has been compromised.

4. A hand-held XRF analyzer comprising:

a housing defining a controlled volume;

a port in the housing for drawing a vacuum in the controlled volume;

a window including a film, the window in front of the controlled volume and sealed with respect to the housing;

a pressure sensor in the controlled volume;

an x-ray source external to the housing and sealed with respect to the housing, for emitting x-rays first into the controlled volume and then through the window to a sample;

a detector external to the housing, sealed with respect to the housing, and responsive to x-rays irradiated by the sample passing through the window and into the controlled volume;

a processor, responsive to the detector, for analyzing irradiated x-rays and also responsive to the pressure sensor for determining if the vacuum in the controlled volume has been compromised;

a hand-held case enclosing the housing, the x-ray source, the detector, and the processor; and an output device controlled by the processor for providing the user with an indication that the vacuum in the controlled volume has been compromised.

* * * * *